(12) United States Patent
Ehringfeld

(10) Patent No.: US 8,742,326 B2
(45) Date of Patent: Jun. 3, 2014

(54) DETERMINATION OF BEAM PARAMETERS FOR ASYMMETRICAL PHOTON BEAMS

(75) Inventor: Christian Ehringfeld, Hohenzollernring (DE)

(73) Assignee: Siemens Aktiengesellschaft, München (DE)

( * ) Notice: Subject to any disclaimer, the term of this patent is extended or adjusted under 35 U.S.C. 154(b) by 979 days.

(21) Appl. No.: 12/845,509

(22) Filed: Jul. 28, 2010

(65) Prior Publication Data

US 2011/0024625 A1    Feb. 3, 2011

(30) Foreign Application Priority Data

Aug. 3, 2009    (DE) .................. 10 2009 035 951

(51) Int. Cl.
*G01J 1/00* (2006.01)
*A61N 5/00* (2006.01)
*A61N 5/10* (2006.01)
*G01N 23/225* (2006.01)

(52) U.S. Cl.
CPC ............... *A61N 5/00* (2013.01); *A61N 5/1075* (2013.01); *A61N 5/1048* (2013.01); *G01N 23/225* (2013.01)
USPC .................................... 250/252.1; 250/336.2

(58) Field of Classification Search
CPC ............ H01J 37/28; H01J 2237/2817; G01N 23/225; A61N 5/1048; A61N 5/1075
USPC ........................................................ 250/252.1
See application file for complete search history.

(56) References Cited

U.S. PATENT DOCUMENTS

2002/0181660 A1* 12/2002 Reinstein et al. .............. 378/205
2005/0045821 A1* 3/2005 Noji et al. ..................... 250/311

FOREIGN PATENT DOCUMENTS

WO    WO 9835358 A1    8/1998

OTHER PUBLICATIONS

German Office Action dated Aug. 4, 2010 for corresponding German Patent Application No. DE 10 2009 035 951.6 with English translation.
Metcalfe, P. et al., "Dosimetry of 6-MV x-ray beam penumbra," Med. Phys. 20 (5), Sep./Oct. 1993, Am. Assoc. Phys. Med., pp. 1439-1445.

* cited by examiner

*Primary Examiner* — Marcus Taningco
(74) *Attorney, Agent, or Firm* — Lempia Summerfield Katz LLC

(57) ABSTRACT

An apparatus and a method for determining a beam parameter of an asymmetrical photon beam generated by an accelerator are provided. A beam profile of a symmetrical photon beam is measured and normalized. For the asymmetrical photon beam, a normalization of the beam profile is implemented such that the maximum of the profile corresponds to a value of the normalized symmetrical beam profile at the site of the maximum. The parameter determination takes place using a conventional beam parameter definition.

12 Claims, 8 Drawing Sheets

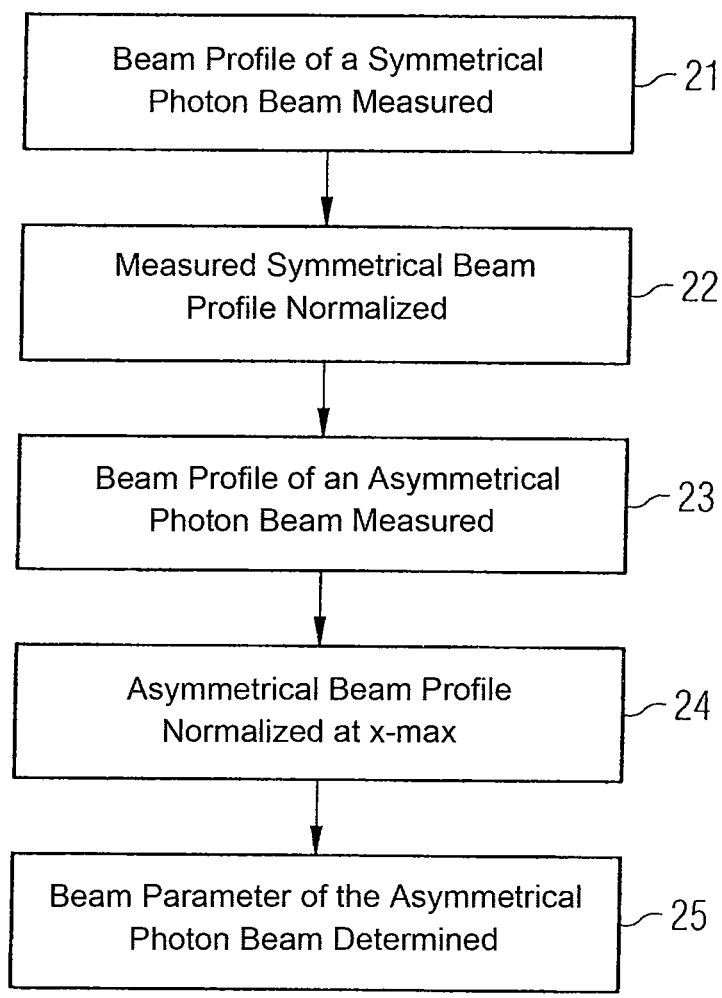

DETERMINATION OF BEAM PARAMETERS FOR ASYMMETRICAL PHOTON BEAMS

This application claims the benefit of DE 10 2009 035 951.6 filed Aug. 3, 2009, which is hereby incorporated by reference.

BACKGROUND

The present embodiments relate to a method and an apparatus for determining a beam parameter of an asymmetrical photon beam generated by an accelerator.

Accelerators are used in the field of medicine for beam generation. Linear accelerators (Linacs) may be used. Linacs generate electrons or, as secondary and/or braking radiation, photons for the used beam. The generated beam may be used for both diagnostic and therapeutic purposes.

Depending on the requirements specified by the respective application, the beam of the accelerator is shaped differently. The shaping may be performed using collimation and absorption. Aside from symmetrical beam profiles (e.g., with respect to a central axis of symmetrical beams), which may result in a dose profile that is symmetrical with respect to an isocenter, asymmetrical beams are also used. For example, numerous small fields are used instead of an expanded field in beam therapy in modern irradiation techniques such as Intensity Modulated Radio Therapy (IMRT). The numerous small fields surround a tumor to be destroyed and produce a better dose distribution in the tumor.

One procedure for generating asymmetrical beams is specified in WO 98/35358, for example.

The asymmetrical beams are described and/or classified for the use.

Parameters are defined for beam description purposes. The parameters are used almost continuously in the accelerator technique. These parameters include the parameter field size (field size and/or field expansion), penumbra, symmetry and flatness. With asymmetrical fields, a displacement of the field may be performed for evaluation and/or analysis purposes such that the center of the field of the asymmetrical field lies on the central axis.

SUMMARY AND DESCRIPTION

The present embodiments may obviate one or more of the drawbacks or limitations in the related art. For example, a method and an apparatus for an improved parameter determination for asymmetrical photon beams may be specified.

In accordance with the present embodiments, a determination of a beam parameter (e.g. field expansion, penumbra or symmetry) of an asymmetrical photon beam generated by an accelerator is performed using measured beam profiles. A measurement of a beam profile of a symmetrical photon beam (e.g., in a plane at right angles to the propagation direction of the beam) is performed (the measured dose distribution in the measurement area is the beam profile). The control parameters of the accelerator (e.g., beam collimation) are adjusted such that the symmetrical photon beam has a maximum field expansion. The symmetrical beam profile thus obtained is normalized (e.g., a normalization to 100% of the central beam and/or the isodose, the dose value at the intersection point of the measurement region with the central axis) and conventional. The normalized symmetrical beam profile may be used for a parameter determination of different asymmetrical beams (i.e., the generation of such a profile). The normalized symmetrical beam profile may function as a type of calibration profile for asymmetrical dose distributions and is generally sufficient. A measured beam profile of an asymmetrical photon beam is normalized such that the maximum of the profile corresponds to a value of the normalized beam profile at the site of the maximum of the asymmetrical beam profile. This value may be a percentage, for example, in the case of a normalization of the isodose of the symmetrical beam to 100%.

The beam parameter may be obtained from the normalized asymmetrical beam using a conventional beam parameter definition. The normalized asymmetrical beam profile may be displaced such that the maximum comes to rest on the central axis (e.g., this may be implemented during the determination of the parameter symmetry).

The present embodiments also include an apparatus and/or apparatus elements for implementing the methods described above. A measuring device for measuring beam dose values is included in the plane at right angles to the propagation direction of the beam. Commercial measuring apparatuses may be used as measuring devices (e.g., a cylindrical ionization chamber or 2D scanning arrays such as the SLA 48 scanning device with an LA 48 matrix by the company PTW). In addition, at least one computing unit is provided for normalizing the beam dose values. The at least one computing unit is configured for the procedure of the present embodiments. The computing unit may be a PC or a work station, for example, configured to assume functions for additional processes (e.g., control, regulation of used medical facilities).

BRIEF DESCRIPTION OF THE DRAWINGS

FIG. 8 shows a flow chart of one embodiment of a method for determining a beam parameter of an asymmetrical photon beam generated by an accelerator.

DETAILED DESCRIPTION OF THE DRAWINGS

Figure 1:
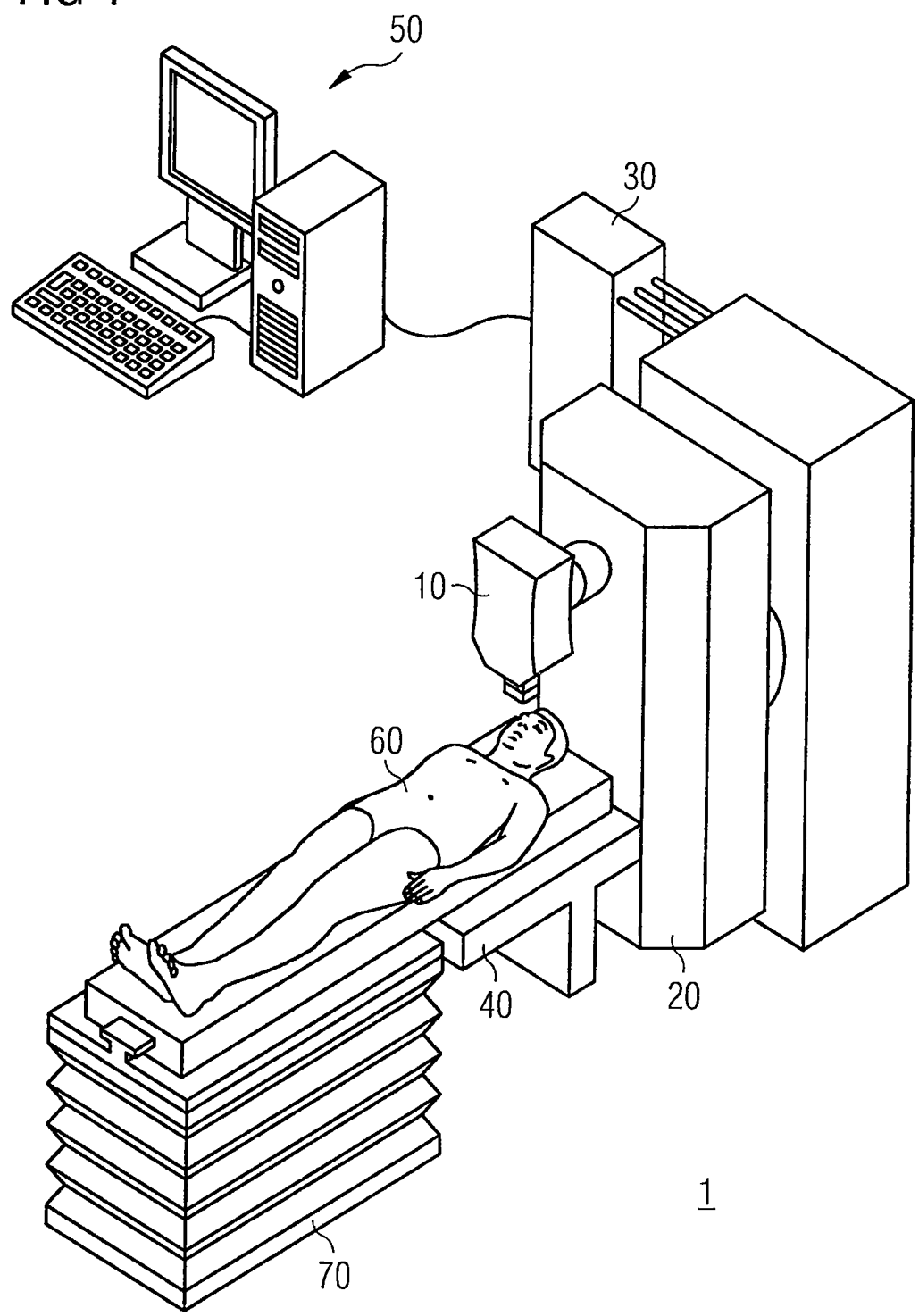
FIG. 1 shows a treatment room with an accelerator.

FIG. 1 shows features of a treatment room 1. A housing of a linear accelerator 10, which is fastened to a rotatable gantry 20, is located in the treatment room 1. The energy supply is illustrated by way of a unit 30, which is connected to an input and control system 50. This input and control system 50 also provides, for example, the computing resources for implementing the method of the present embodiments. A patient table 70 and a patient 60 to be treated and positioned thereupon are also shown in FIG. 1.

Figure 2:
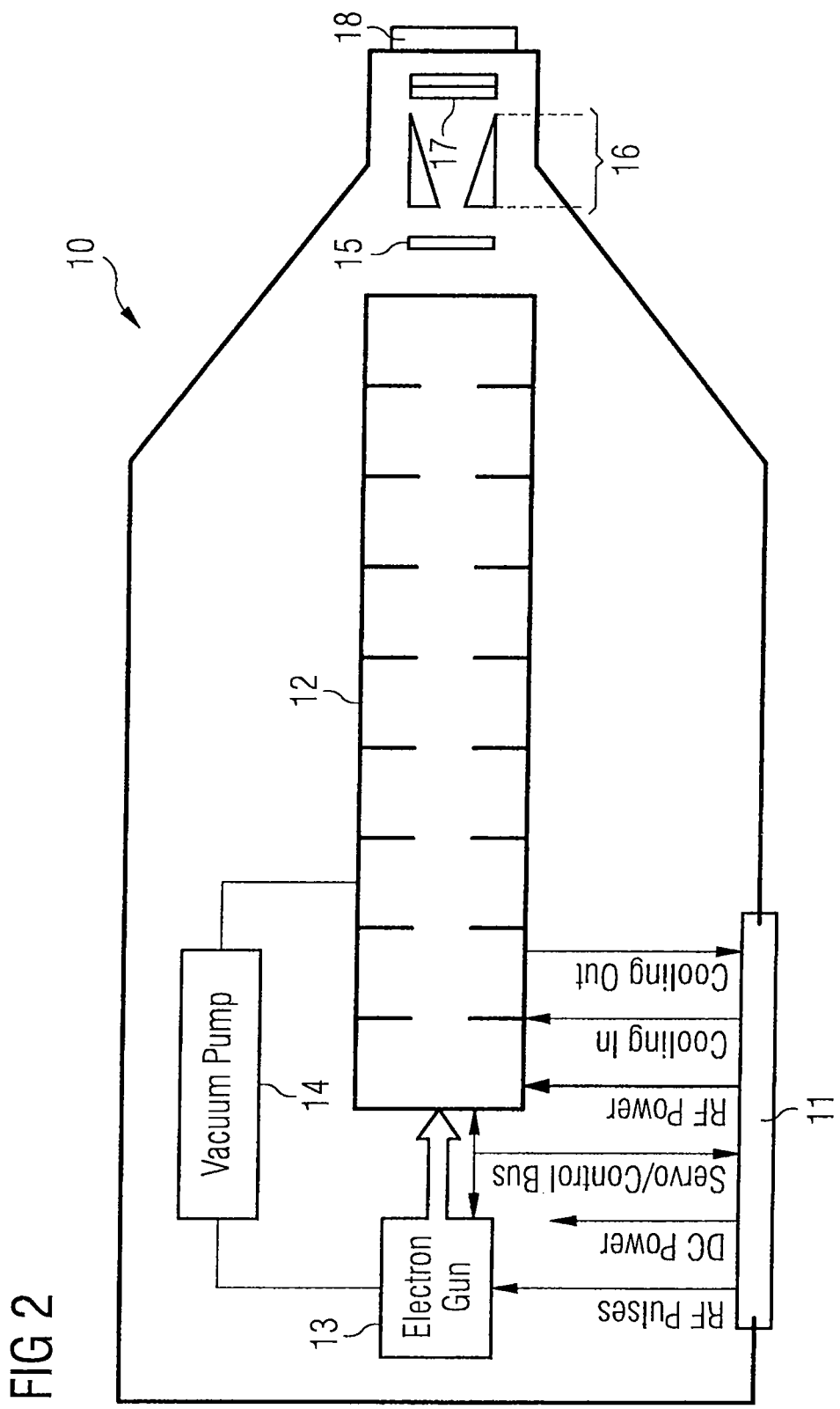
FIG. 2 shows a schematic representation of a linear accelerator.

FIG. 2 shows a schematic representation of the design of a linear accelerator. The linear accelerator includes a control interface 11, an electronic source 13, a system 12 for guiding and accelerating electrons, a vacuum pump 14, a target 15, a collimator 16, a dosimeter 17 and fastening brackets 18. The housing 10 of the accelerator may be coated with material that shields magnetic fields and radiation in order to shield the internal elements. The electrons generated by the electron source 13 reach the target 15 using the system for guiding and accelerating electrons 12. In one embodiment, the target 15 is made of a material with a high atomic mass (e.g., gold or wolfram). Upon impact and braking of the electronic beam, a photon beam is generated, the photon beam having an energy spectrum that is suited to the radiation treatment. The bracket 18 may be used to attach a smoothing filter or absorption structures for beam formation, for example.

A linear accelerator may initially generate, as in FIG. 2, a beam that is symmetrical with respect to a central axis and/or an axis of symmetry of the linear accelerator. Asymmetrical beams may be shaped using collimation and/or absorption.

Figure 3:
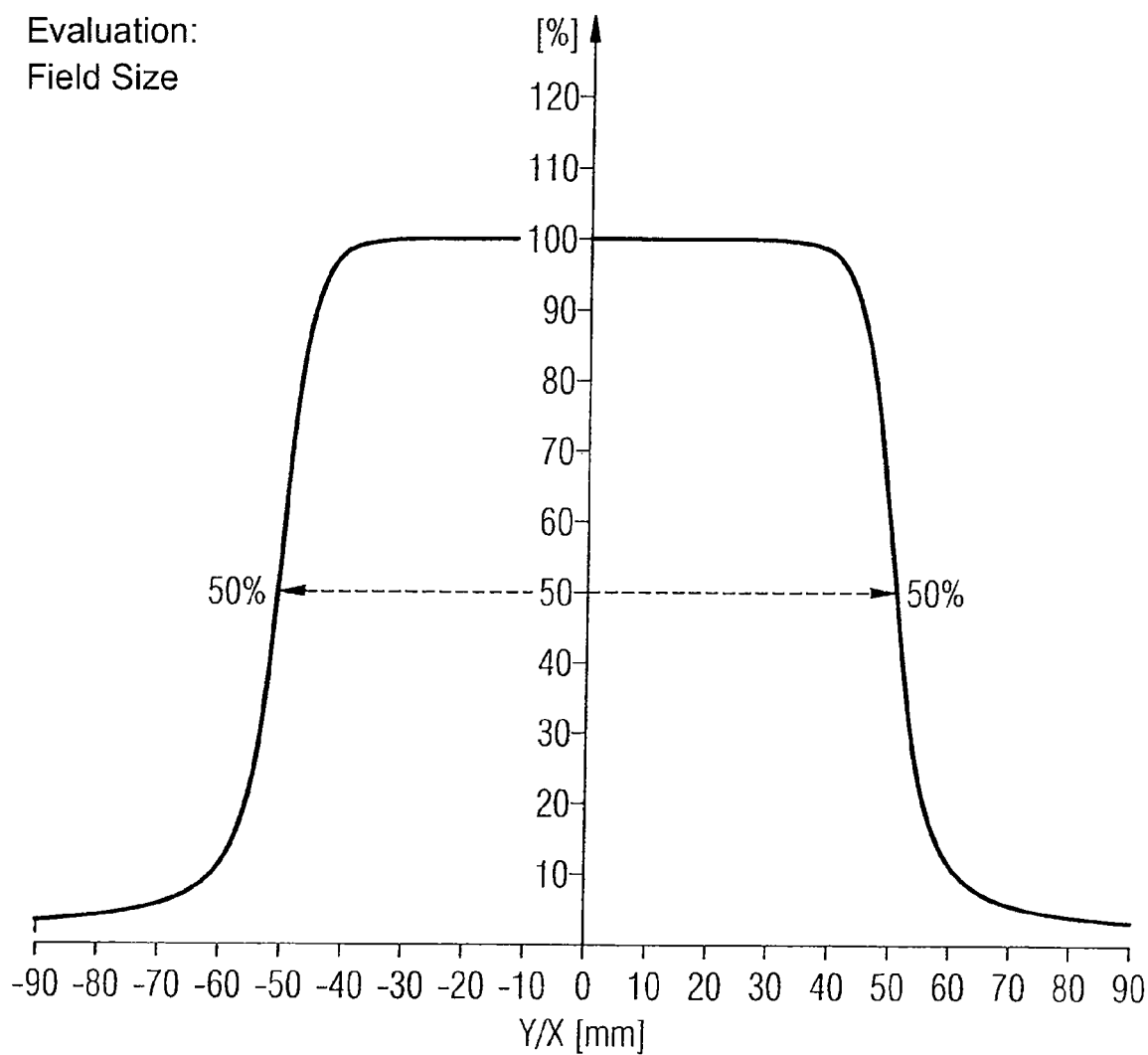
FIG. 3 shows a representation for defining the parameter field size.
Figure 4:
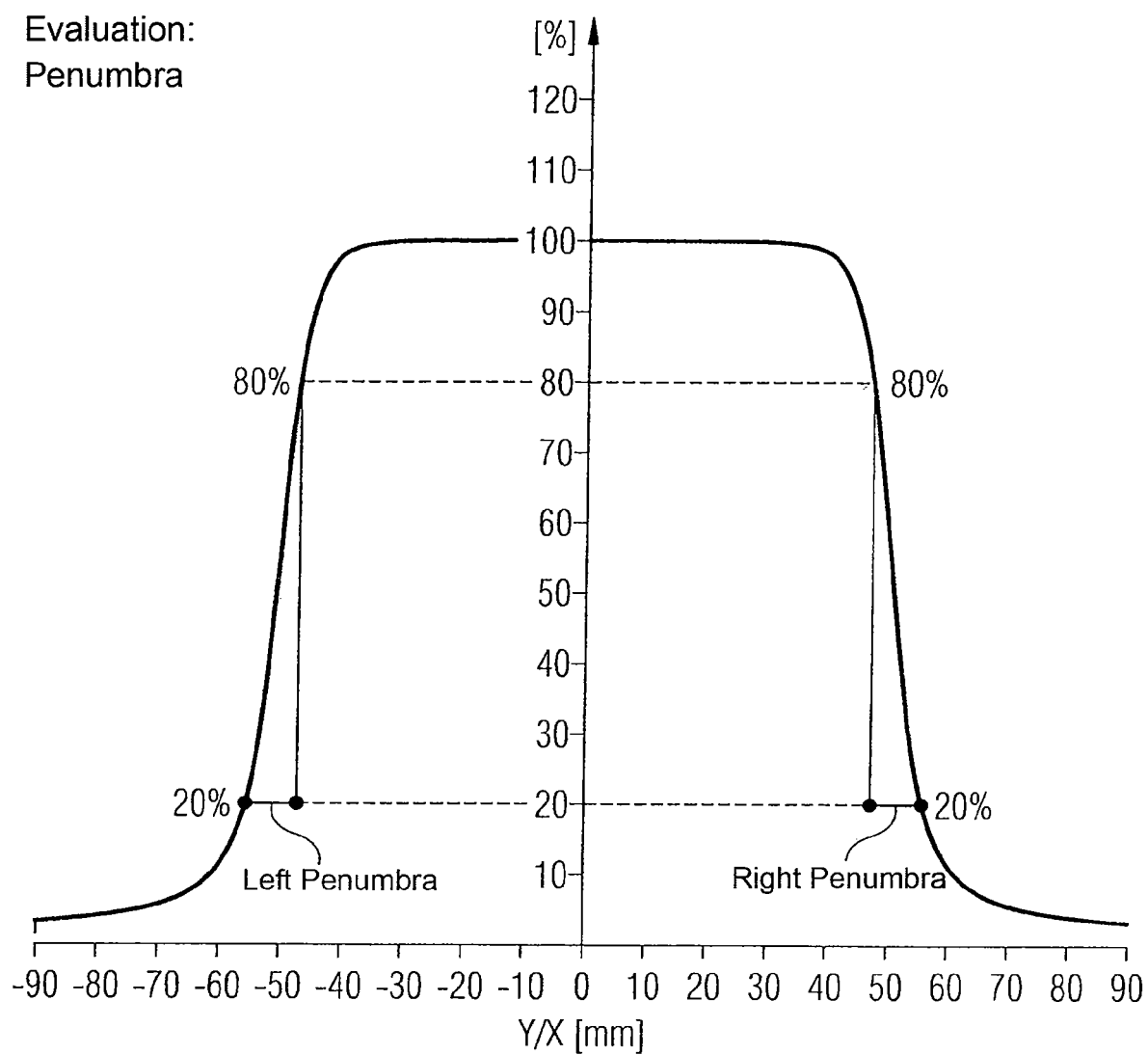
FIG. 4 shows a representation for defining the parameter penumbra.
Figure 5:
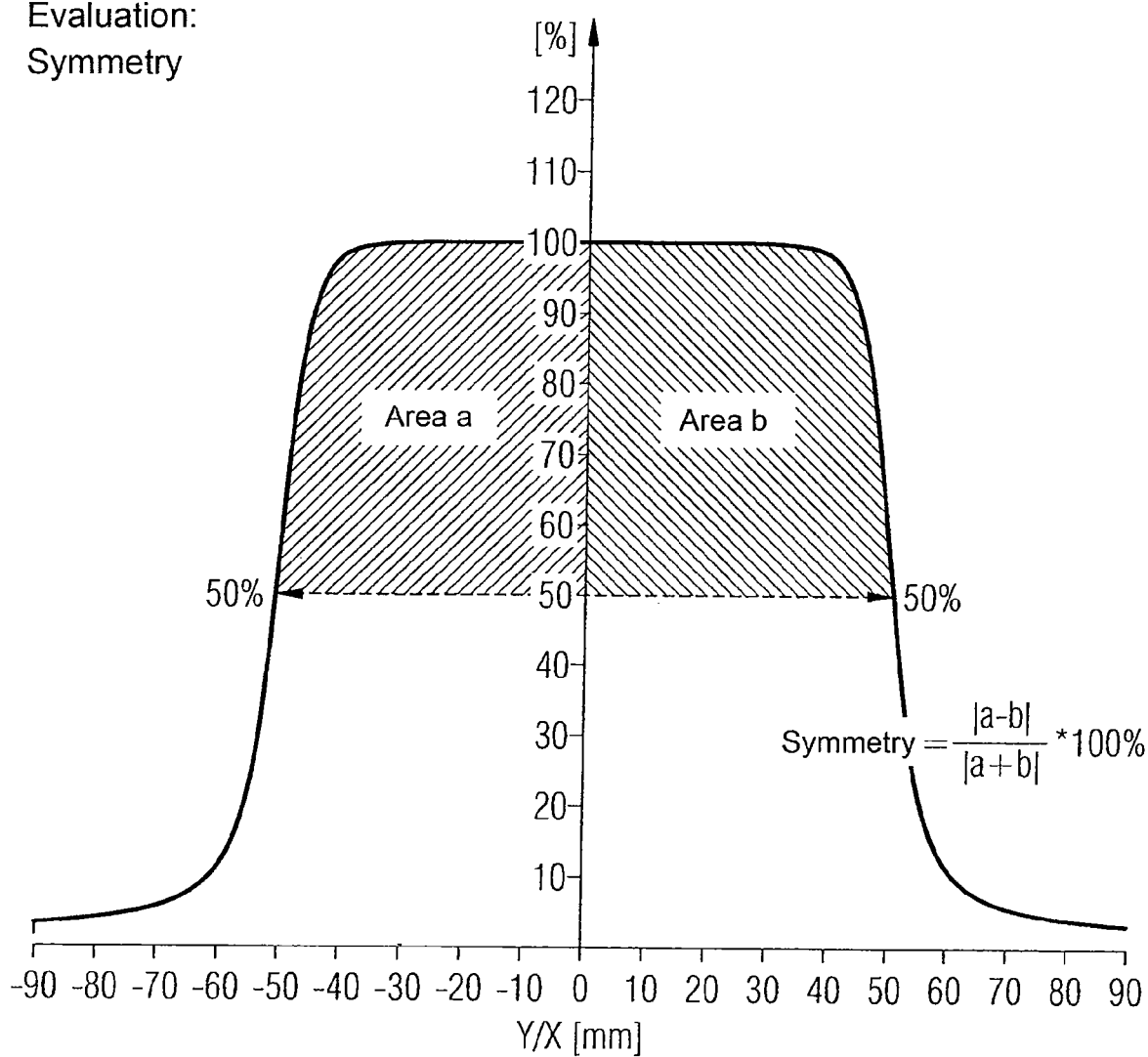
FIG. 5 shows a representation for defining the parameter symmetry.

Typical beam parameters of a beam generated by an accelerator are field size or expansion (field size), penumbra (half shade), symmetry and flatness. Definitions exist for these parameters, which are used generally. For example, the radiological field size may be defined by the drop to 50% of the maximum intensity (50% isodose). In other words, the radiological field size may be defined as the distance of the 50% dose between the left and right sides of the profile (e.g., as illustrated in FIG. 3). Another beam parameter is penumbra or half shade, which is the distance between the 20% and 80% intensity values and/or isodose on both sides of the profile (e.g., as illustrated in FIG. 4). In other words, the parameter penumbra measures how quickly the field drops from 80% intensity to 20% intensity and/or how clearly the field expansion is defined. Thus, the penumbra parameter also provides a measure of accuracy of the value for the field expansion. The symmetry may be defined as $100\% \times |a-b|/|a+b|$, with "a" being the area to the left of the central axis and "b" being the area to the right of the central axis (e.g., as illustrated in FIG. 5). The areas a and b are restricted by the central axis and the 50% field boundary.

Figure 6:
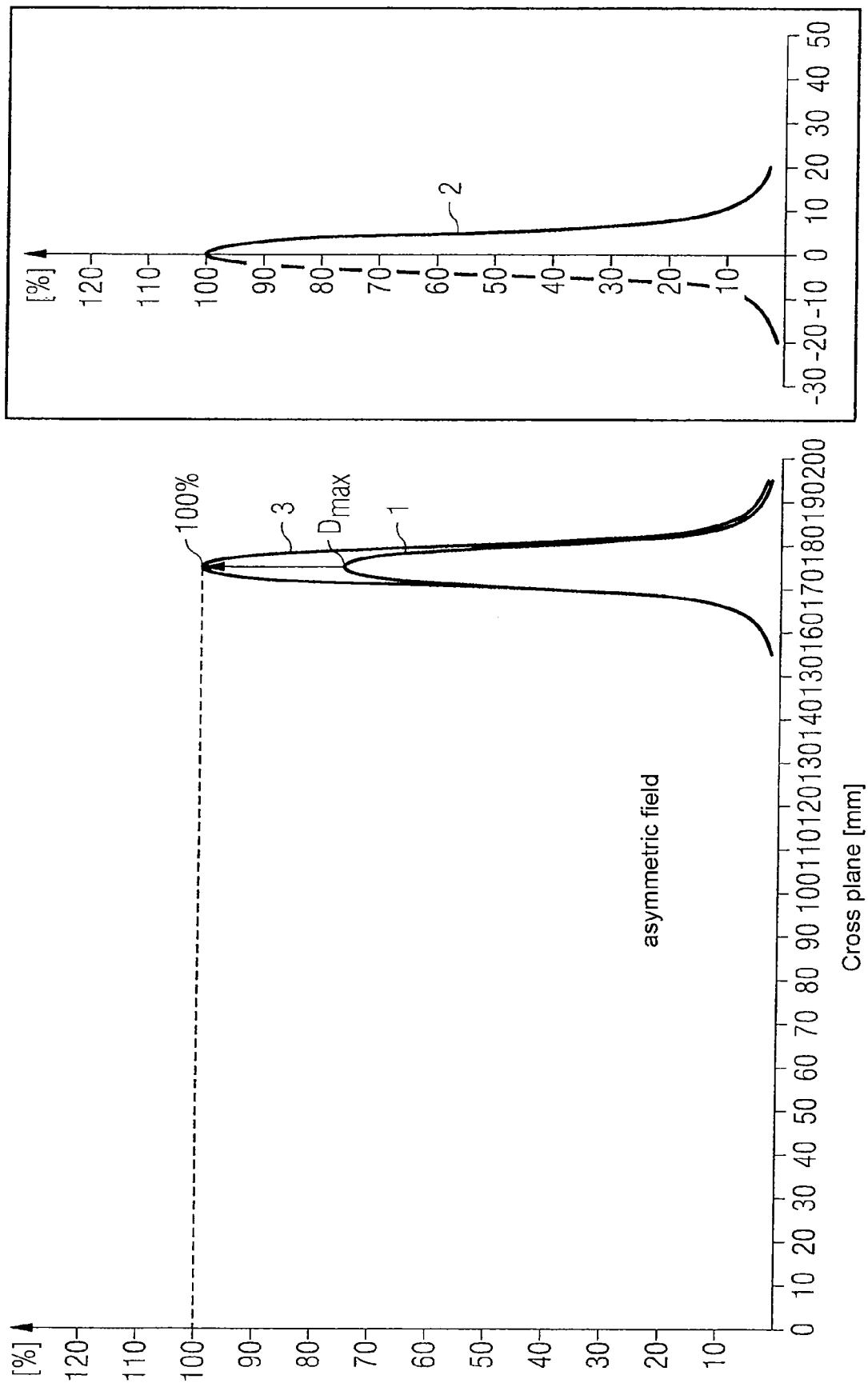
FIG. 6 shows a conventional normalization of beam dose values of an asymmetrical beam.

FIG. 6 shows a conventional procedure for rescaling. An asymmetrical curve 1 with a maximum intensity value $D_{max}$ is displaced for analysis in the evaluation software (act 2) such that the center of the field of the asymmetrical field lies on the central axis and may thus be scaled to 100% (act 3).

This method is an approximation with flaws (e.g., with respect to the evaluation of the radiological field expansion). In particular, the flaws concern the parameters of field size, penumbra and symmetry.

Figure 7:
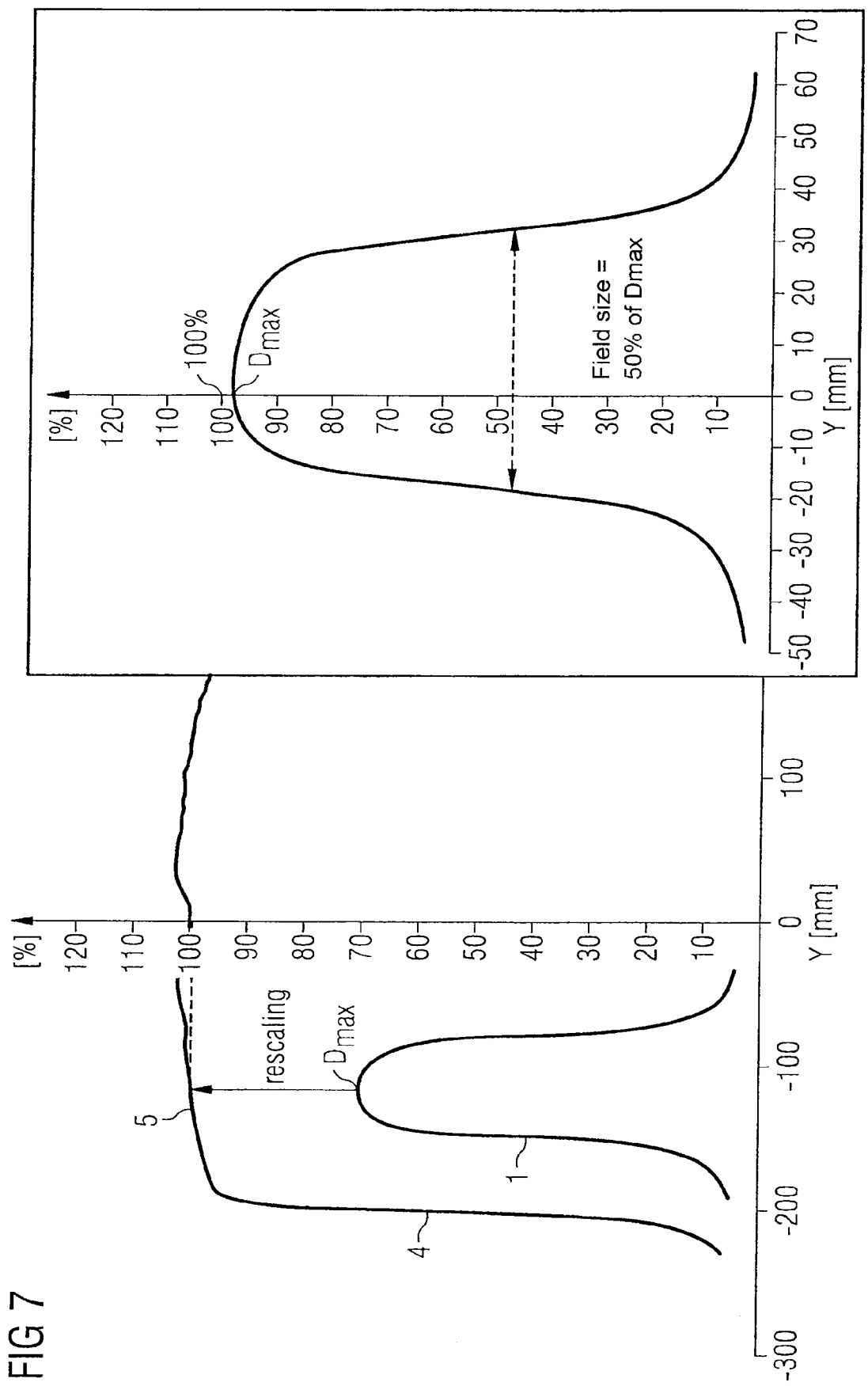
FIG. 7 shows one embodiment of a normalization of beam dose values of an asymmetrical beam.

One embodiment of a method for normalizing beam dose values of an asymmetrical beam, described with the aid of FIG. 7, offers an improvement.

FIG. 7 also shows the asymmetrical field distribution 1 from FIG. 3. A symmetrical field distribution 4 is also shown. This was obtained using a measurement with the maximum field expansion of 40×40 cm and was then scaled to 100% in the case of the central axis. The asymmetrical curve is normalized in act 5 to the value of the symmetrical field distribution 4 at the site $x_{max}$ of the maximum of the asymmetrical curve. This rescaling provides more accurate values during the parameter determination. For the parameter determination (e.g., parameter symmetry), a displacement of the rescaled curve may take place (also shown in FIG. 7).

FIG. 8 shows one embodiment of a method for determining a beam parameter of an asymmetrical photon beam generated by an accelerator. The method includes the acts of: measuring a beam profile of a symmetrical photon beam (act 21); normalizing the measured symmetrical beam profile (act 22); measuring a beam profile of the asymmetrical photon beam (act 23); normalizing the beam profile of the asymmetrical photon beam such that the maximum of the profile corresponds to the value of the normalized symmetrical beam profile at the site of the maximum (act 24); and determining the beam parameter of the asymmetrical beam using a conventional beam parameter definition (act 25).

The sequence of acts may be different than that specified in FIG. 8. In one embodiment, the sequence of measurements may be interchanged from the symmetrical and asymmetrical profile.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for determining a beam parameter of an asymmetrical photon beam generated by an accelerator, the method comprising:
   measuring a beam profile of a symmetrical photon beam;
   normalizing the measured symmetrical beam profile;
   measuring a beam profile of the asymmetrical photon beam;
   normalizing the beam profile of the asymmetrical photon beam such that the maximum of the asymmetrical beam profile corresponds to a value of the normalized symmetrical beam profile at the site of the maximum; and
   determining the beam parameter of the asymmetrical beam,
   wherein the symmetrical photon beam has a maximum field expansion.

2. The method as claimed in claim 1, wherein the normalized beam profile of the asymmetrical photon beam is moved to a central axis of the symmetrical beam for parameter determination.

3. The method as claimed in claim 2, wherein the beam profile of the symmetrical beam is normalized to 100% at the central axis of the beam.

4. The method as claimed in claim 3, wherein the beam parameter is a parameter that is also used for symmetrical beams.

5. The method as claimed in claim 3, further comprising determining the beam parameter of field expansion, penumbra or symmetry.

6. The method as claimed in claim 2, wherein the beam parameter is a parameter that is also used for symmetrical beams.

7. The method as claimed in claim 2, further comprising determining the beam parameter of field expansion, penumbra or symmetry.

8. The method as claimed in claim 1, wherein the beam parameter is a parameter that is also used for symmetrical beams.

9. The method as claimed in claim 8, further comprising determining the beam parameter of field expansion, penumbra or symmetry.

10. The method as claimed in claim 1, further comprising determining the beam parameter of field expansion, penumbra or symmetry.

11. An apparatus for determining a beam parameter of an asymmetrical photon beam generated by an accelerator, the apparatus comprising:
    a measuring device for measuring a beam profile of a symmetrical photon beam;
    a measuring device for measuring a beam profile of the asymmetrical photon beam; and
    a computing unit configured to:
       normalize the measured symmetrical beam profile;
       normalize the beam profile of the asymmetrical photon beam such that the maximum of the asymmetrical beam profile corresponds to a value of the normalized symmetrical beam profile at the site of the maximum; and determine the beam parameter of the asymmetrical beam, wherein the symmetrical photon beam has a maximum field expansion.

12. The apparatus as claimed in claim 11, wherein the computing unit is configured to move the normalized beam profile of the asymmetrical photon beam to a central axis of the symmetrical beam for parameter determination.

* * * * *